(12) United States Patent
Thadani et al.

(10) Patent No.: US 7,867,989 B2
(45) Date of Patent: Jan. 11, 2011

(54) α-GLUCOSIDASE INHIBITORS FROM LICHENS

(76) Inventors: Vinitha Moolchand Thadani, Department of Chemistry, University of Peradenia, Peradeniya (LK); Shamsun Nahar Khan, HEJ Research Institute, University of Karachi, Karachi (PK); Veranja Karunratne, 37/3 Aniwatta Road, Kandy (LK); Muhammad Iqbal Choudhary, HEJ Research Institute, Karachi University, Karachi (PK)

( * ) Notice: Subject to any disclaimer, the term of this patent is extended or adjusted under 35 U.S.C. 154(b) by 570 days.

(21) Appl. No.: 11/767,465

(22) Filed: Jun. 22, 2007

(65) Prior Publication Data
US 2008/0318916 A1    Dec. 25, 2008

(51) Int. Cl.
*A61K 31/56* (2006.01)

(52) U.S. Cl. ...................................................... 514/178

(58) Field of Classification Search ................... 514/178
See application file for complete search history.

(56) References Cited

U.S. PATENT DOCUMENTS
4,536,474 A *  8/1985  Yamamoto et al. ............ 435/42

OTHER PUBLICATIONS
Ageta et al. "Fern constituents. on the origin of a Formosan native drug "Tie-Yu-san" and its triterpenoid constituents," Shoyakugaku Zasshi, 1981, vol. 35, No. 4, pp. 259-261. CAPLUS abstract, AN 1982:411686.*

* cited by examiner

*Primary Examiner*—Shengjun Wang

(57) ABSTRACT

This invention is directed to a novel method for the inhibition of α-glucosidase enzyme and thus treating diabetes, viral infections, fungal infections, autoimmune function disorders and obesity using compounds derived as lichen metabolites; more specifically, this includes the therapeutic applications of methylorsellinate (2,4-dihydroxy-6-methylbenzoate, Compound I), methyl-β-orinolcarboxylate (2,4-dihydroxy-3,6-dimethylbenzoate, Compound II) and zeorin (6,22-hopanediol, Compound III).

3 Claims, 3 Drawing Sheets

Compound III

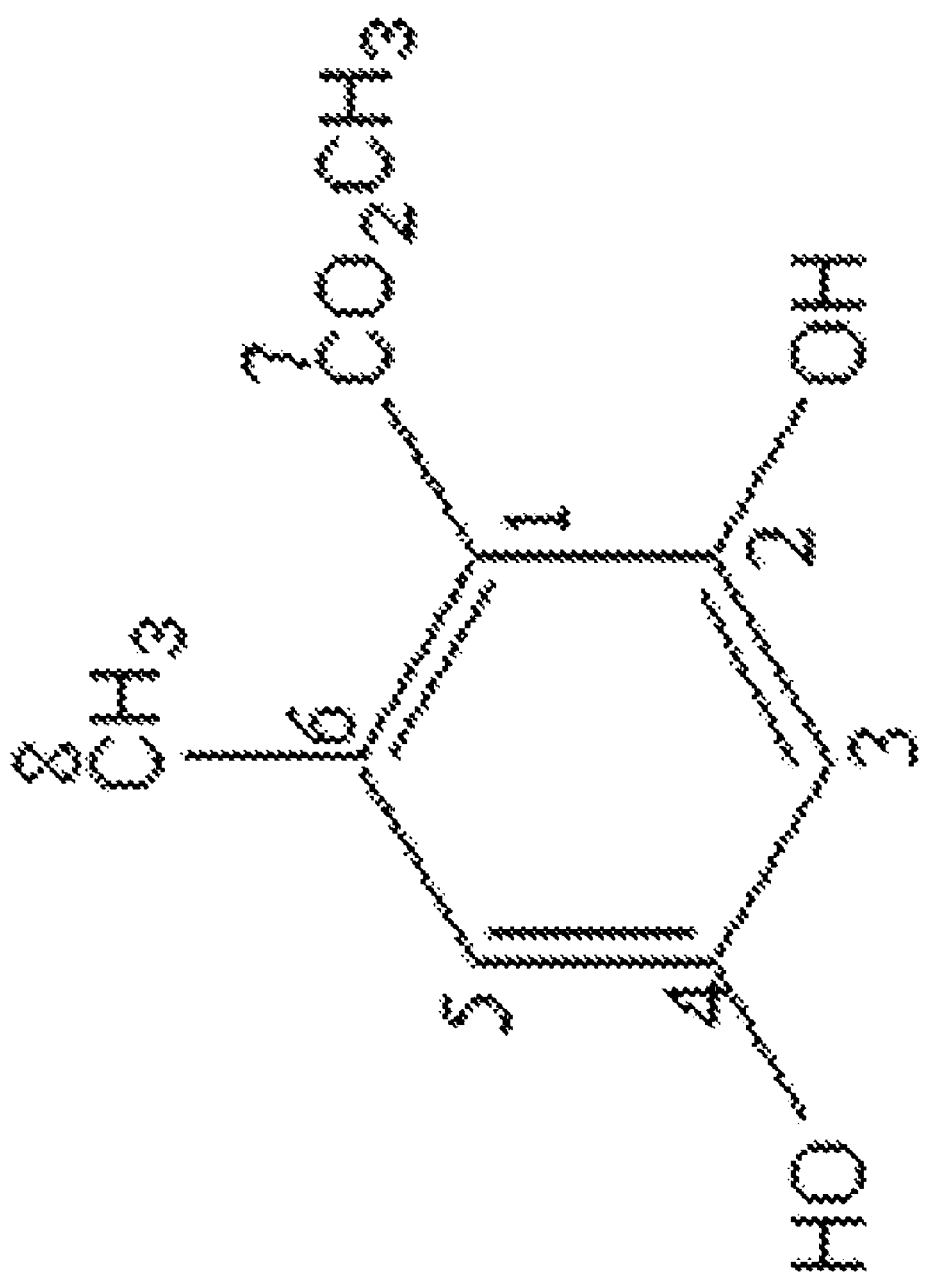
Fig. 1, Compound I

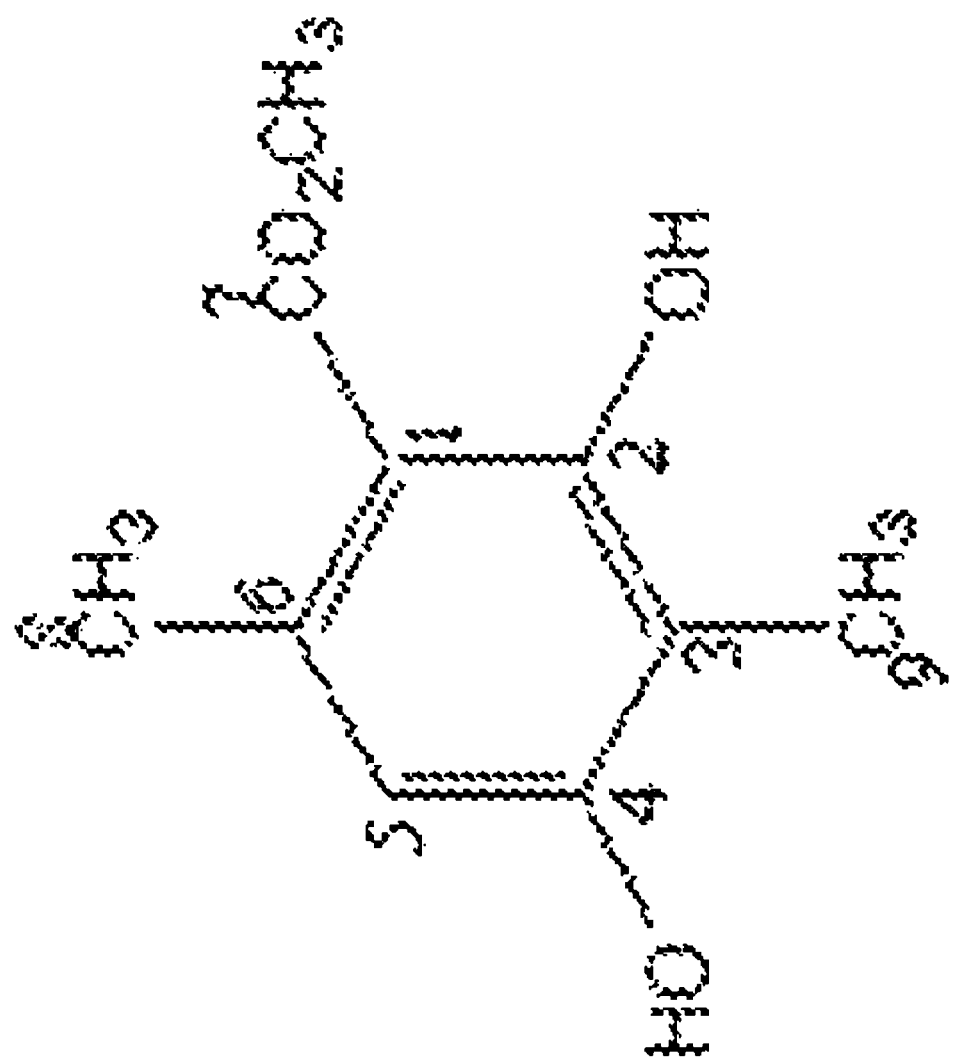
Fig. 2. Compound II

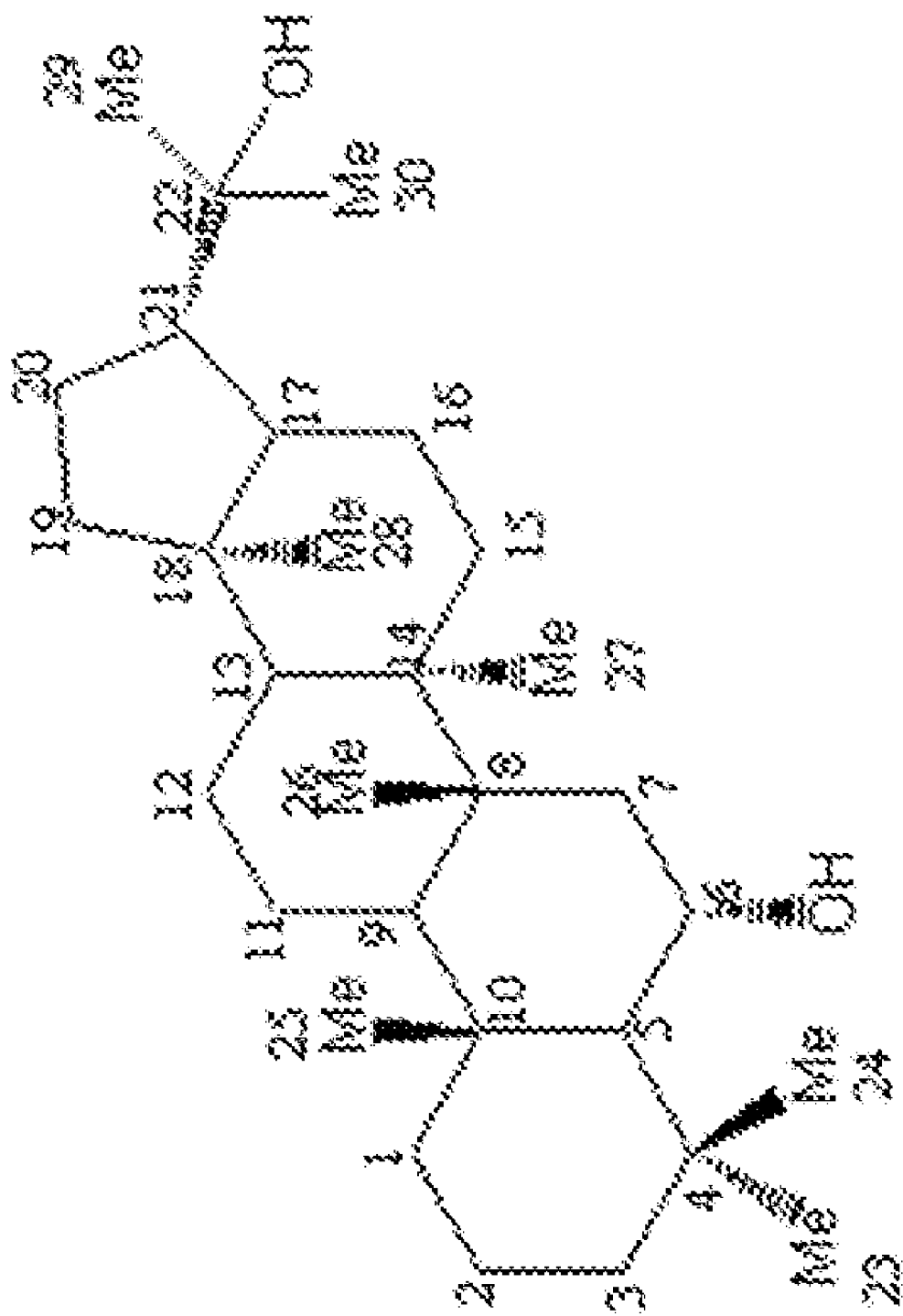
Fig. 3. Compound III

α-GLUCOSIDASE INHIBITORS FROM LICHENS

BACKGROUND

Glucosidase enzymes are involved in several biological processes such as the intestinal digestion, the biosynthesis of glycoproteins and the lysosomal catabolism of the glycoconjugates (Homonojirimycin isomers and N-alkylated homonojirimycins: structural and conformational basis of inhibition of glycosidases. Asano N, Nishida M, Kato A, Matsui K, Shimada Y, Itoh T, Baba M, Watson A A, Nash R J, Lilley P M, Watkin D J, Fleet G W, J Med Chem. 1998 Jul. 2; 41(14):2565-71). Intestinal α-glucosidases are involved in the final step of the carbohydrate digestion to convert these into monosaccharides which are absorbed from the intestine.

As a result of the catalysis produced by α-glucosidase enzyme in the final step in the digestive process of carbohydrates, its inhibitors can retard the uptake of dietary carbohydrates and suppress postprandial hyperglycemia, and could be useful to treat diabetic and/or obese patients [Novel α-glucosidase Inhibitors with a tetrachlorophthalimide Skeleton., S. Sou, S. Mayumi, H. Takahashi, R. Yamasak, S. Kadoya, M. Sodeoka, and Y. Hashimoto, *Bioorg. Med. Chem. Lett.,* 2000, 10, 1081].

The α-glucosidase inhibitors are effective in lowering the insulin release, insulin requirement and some can lower plasma lipids. The acarbose is a very widely prescribed drug in the management of the type II diabetes and recently a U.S. Pat. No. 6,387,361 to Rosner describes the use of acarbose in the treatment of obesity. According to the criteria issued by WHO (World Health Organization) based on a glucose tolerance test, diabetes mellitus and impaired glucose tolerance (hereinafter sometimes referred to as IGT) are distinguished by the fasting blood glucose level and the blood glucose level 2 hours after glucose loading. Patients with IGT have high blood glucose levels compared to those of patients with diabetes mellitus, and are reported to be at increased risk of developing diabetes mellitus and complications of arteriosclerotic diseases. In particular, it is known that patients with IGT who have blood glucose levels of 170 mg/dl or above at 2 hours following glucose loading, i.e., patients with high-risk IGT, may develop diabetes mellitus at a high rate [Diabetes Frontier, p. 136, 1992]. With regard to voglibose which is an α-glucosidase inhibitor, there are reports of studies on effects of voglibose for insulin-resistant IGT and diabetes [Yakuri-to-Chiryo (Japanese Pharmacology & Therapeutics), 24 (5):213 (1996); Metabol. Exp. Clin., 45:731, 1996]. Voglibose (AO-128) is also known to have effects of lowering blood glucose level and improving glucose tolerance in rats [Yakuri-to-Chiryo (Japanese Pharmacology & Therapeutics), 19 (11):161 (1991); Journal of Nutrition Science and Vitaminology, 45 (1):33 (1992)]. On the contrary, it has also been reported that the effect of voglibose in improving glucose tolerance could not be verified in human [Rinsho-Seijinbyo, 22 (4): 109 (1992)]. An antibiotic pradimicin Q as α-glucosidase inhibitor is described in the U.S. Pat. No. 5,091,418 to Swada.

In addition, they have also been used as antiobesity drugs, fungistatic compounds, insect antifeedents, antivirals and immune modulators [Glycosidase inhibitors and their chemotherapeutic value, Part 1. el Ashry E S, Rashed N, Shobier A H., Pharmazie. 2000 April; 55(4):251-620]. The antiviral activity due to inhibition of α-glucosidase results from abnormal functionality of glycoproteins because of incomplete modification of glycans. Suppression of this process is the basis of antiviral activity [A glucosidase-Inhibitors as potential broad based antiviral agents, Anand Mehta, Nicole Zitzmann, Pauline M. Rudd, Timothy M. Block, Raymond A. Dwek, Febs Letters 430 (1998)17-22] and decrease in growth rate of tumors [Inhibition of experimental metastasis by an alpha-glucosidase inhibitor, 1,6-epi-cyclophellitol. Atsumi S, Nosaka C, Ochi Y, Iinuma H, Umezawa K. Cancer Res. 1993 Oct. 15; 53(20):4896-9]. The α-glucosidase inhibitor N-(1, 3-dihydroxy-2-propyl)valiolamine is described as a promoter of calcium absorption in the U.S. Pat. No. 5,036,081.

Lichens are small perennial plants consisting of a symbiotic association of a fungus and an alga. They produce characteristic secondary metabolites that are unique with respect to those of higher plants. Several lichen extracts have been used for various remedies in folk medicine, and screening test with lichens have indicated the frequent occurrence of metabolites with antibiotic (Cavallito, C. J.; Fruehauf, D. M.; Bailey, J. H. *J. Am. Chem. Soc.* 1948, 70, 3724-3726), antimycobacterial, (Ingolfsdottir, K.; Chung, G. A. C.; Skulason, V. G.; Gissurarson, S. R.; Vilhelmsdottir, M. *Eur. J. Pharm. Sci.* 1998, 6, 141-144), antiviral (Yamamoto, Y.; Miura, Y.; Kinoshita, Y.; Higuchi, M.; Yamada, Y.; Murakami, A.; Ohigashi, H.; Koshimizu, K. *Chem. Pharm. Bull.* 1995, 43, 1388-1390; Neamati, N.; Hong, H.; Mazumder, A.; Wang, S.; Sunder, S.; Nicklaus, M. C.; Milne, G. W.; Proksa, B.; Pommier, Y. *J. Med. Chem.* 1997, 40, 942-951), analgesic and antipyretic properties (Okuyama, E.; Umeyama, K.; Yamazaki, M.; Kinoshita, Y.; Yamamoto, Y. *Planta Med.* 1995, 61, 113-115). Other literature reports of biological activities of these naturally occurring compounds are scarce, thus the therapeutic potential of lichens remain largely unexplored. This may partly be due to the difficulties encountered with collecting substantial amounts of plant material, as most of the lichen species grow as scattered patches, mainly on stones or on tree trunks. The study of bioactivities of lichen compounds is important because the secondary metabolites of lichens are found almost exclusively only in lichens. Out of the ≈700 secondary metabolites know up to 80% are restricted to the lichenized state. (Huneck, S. and Yoshimura, I. 1996, *Identification of Lichen substances.* Springer). Furthermore these distinct classes of lichen metabolites have not been fully tested for their enzyme inhibitory assays.

Herein we report the surprising α-glucosidase inhibition activity of three lichen metabolites that can be used as potent α-glucosidase inhibitor and thus in a therapeutic modality in a variety of medical applications as described above. These include Methylorsellinate or 2,4-dihydroxy-6-methylbenzoate (Compound I) isolated from *Parmotrema grayana*, and *Roccella montagnei* reported from *Pseudocyphellaria crocata* (L.) Vain (Maass, W. S. G.; *Can. J. Bot.,* 1975b, 53, 1031-1039) Methyl-β-orinolcarboxylate or 2,4-dihydroxy-3, 6-dimethylbenzoate (Compound II) isolated from *Cladonia* sp. reported from *Stereocaulan alpinum* Laur., (Hylands, P. J.; Ingolfsdottir, K.; *Phytochemistry,* 1985, 24, 127-129) and Zeorin or 6,22-Hopanediol (Compound III) (a constituent of various lichens e.g. *Anaptychia, Lecanora, Parmelia, Nephroma, Placodium* sp.) isolated from *Cladonia* sp. Other than the report on isolation of zeorin from *Iris missouriensis* roots (Wong, S. M.; Oshima, Y.; Pezzuto, J. M.; Fong, H. H.; Fransworth, N. R.; *J. Phar. Sci,* 1986, 75(3), 317-320) these compounds are lichen specific.

BRIEF DESCRIPTION OF DRAWINGS

FIG. 1: Chemical Structure of Compound I
FIG. 2: Chemical Structure of Compound II
FIG. 3: Chemical Structure of Compound III

DETAILED DESCRIPTION

Isolation and Identification of Lichen Metabolites

Cleaned, dried lichens were sequentially extracted with $CH_2Cl_2$ followed by methanol. The crude $CH_2Cl_2$ extract and methanol extract were fractionated via silica gel Medium Pressure Liquid Chromatography (MPLC) using accelerating gradient elution with a SEPARO column packed with Merck Kieselgel (230-400 mesh ASTM) and metering pump FM1-pump, model QD OSSY and column chromatography. Depending on the polarity of the compounds to be separated, the combinations of hexane-dichloromethane, hexane-ethyl acetate and dichloromethane-methanol were used as stepwise gradients. Analytical Thin Layer Chromotography (TLC) was carried out on Kieselgel 60 pre-coated aluminum foil plates.

The spots of the TLC plates were detected under UV light (wavelength 254 and 365 nm) and spraying with anisaldehyde. $^1$H NMR, $^{13}$C NMR, COSY, DEPT, HMBC, HMQC, HETCOR and NOESY spectra were recorded on a VARIAN 300 MHz machine at ambient temperature at 30° C. Low and high resolution Electron Impact (EI) mass spectra were recorded on a Kratos/AEI MS-902 spectrometer detector. Fast Atom Bombardment (FAB) mass spectra were measured on a Varian Mat CH 4-B spectrometer using 1-thioglycerol as the matrix.

Identity of the known compounds was done by the comparison of the physical data (TLC, co-TLC and m.p) of those of the authentic samples and the reported spectral data (UV, IR, $^1$H NMR, $^{13}$C NMR, COSY, DEPT, NOESY, HMBC, HMQC, HETCOR and MS).

Purity of the compound was confirmed using analytical HPLC Waters 2690 coupled to U.V. Photodiode Array Detector Waters 996 using a Novapack $C_{18}$ reversed phase column.

Activity Assay

The α-Glucosidase (EC 3.2.1.20) inhibition assay was performed according to the slightly modified method of Oki et al (Oki, T.; Matsui, T.; Osajima, Y. *J. Agric. Food Chem.* 1999, 47, 550-5530. The α-Glucosadase (EC 3.2.1.20) from *Sacchromomyces* sp. was purchased from Wako Pure Chemical Industries Ltd. (Wako 076-02841). The inhibition was measured spectrophotometrically at pH 6.9 and at 37° C. using 0.5 μM p-nitrophenyl α-D-glucopyranoside (PNP-G) as a substrate and 250 units/mL of enzyme, in 50 mM sodium phosphate buffer containing 100 mM NaCl. 1-Deoxynojirimycin (0.425 mM) and acrabose (0.78 mM) were used as positive controls. The increments in absorption at 400 nm due to the hydrolysis of PNP-G by α-glucosidase were monitored continuously with a molecular devices spectrophotometer.

TABLE 1

Percentage inhibition and $IC_{50}$ values of lichen compounds against α-glucosidase enzyme

| Compound | $IC_{50}$ values ± SEM [μM] |
|---|---|
| Methyl orsellinate | 165.0 ± 1.2 |
| Methyl β-orcinol carboxylate | 140.0 ± 0.6 |
| Zeorin | 100.0 ± 0.3 |
| Standard (1-Deoxynojirimycin) | 425.0 ± 8.9 |
| Standard (Acarbose) | 700.0 ± 10.4 |

We claim:

1. A method for inhibition α-glucosidase enzyme in a human or animal in need thereof comprises administering to the human or animal an effective amount of isolated zeorin, wherein the human or animal has diabetes.

2. The method according to claim 1 further comprises administering another glucosidase inhibitor.

3. The method according to claim 1 wherein isolated zeorin is in a pharmaceutically elegant dosage form.

* * * * *